US006350872B1

(12) United States Patent
Virkler et al.

(10) Patent No.: US 6,350,872 B1
(45) Date of Patent: Feb. 26, 2002

(54) SALT FREE DYEING OF CELLULOSIC FIBERS WITH ANIONIC DYES

(75) Inventors: Howard E. Virkler, Charlotte, NC (US); D. M. Lewis, West Yorkshire; Peter J. Broadbent, North Yorkshire, both of (GB)

(73) Assignee: The Virkler Company, Charlotte, NC (US)

( * ) Notice: Subject to any disclaimer, the term of this patent is extended or adjusted under 35 U.S.C. 154(b) by 0 days.

(21) Appl. No.: 09/181,494

(22) Filed: Oct. 28, 1998

(51) Int. Cl.$^7$ .................. C07D 251/30; C07D 251/38; C07D 251/42; C07D 251/48
(52) U.S. Cl. .............. 544/194; 544/204; 544/207; 544/208; 544/210; 544/211; 544/212; 524/100; 8/537; 8/543; 8/544
(58) Field of Search ................ 544/194, 204, 544/207, 208, 210, 211, 212

(56) References Cited

U.S. PATENT DOCUMENTS

| | | | |
|---|---|---|---|
| 3,271,443 A | 9/1966 | Burness | 260/501 |
| 4,180,664 A | 12/1979 | Perrin et al. | 544/194 |
| 4,246,670 A | 1/1981 | Perrin et al. | 8/566 |
| 4,313,732 A | 2/1982 | Teague et al. | 8/541 |
| 4,362,874 A | 12/1982 | Kalk et al. | 544/317 |
| 4,695,632 A | 9/1987 | Kalk et al. | 544/194 |
| 5,330,541 A | 7/1994 | Hall et al. | 8/576 |
| 5,346,510 A | 9/1994 | Krallmann et al. | 8/638 |
| 5,348,557 A | 9/1994 | von der Eltz et al. | 8/188 |
| 5,489,313 A | 2/1996 | Hall et al. | 8/543 |
| 5,741,905 A | 4/1998 | Bacher et al. | 544/194 |

FOREIGN PATENT DOCUMENTS

GB    2 119 367    * 11/1983

OTHER PUBLICATIONS

"Quat 188 Cationic Reagent: For Modifying Polymers To Product Quaternary Ammonium Compounds," *Dow USA, An Operating Unit of the Dow Chemical Company, Performance Products Department*, Jan. 22, 1992.

* cited by examiner

*Primary Examiner*—Richard L. Raymond
*Assistant Examiner*—Venkataraman Balasubramanian
(74) *Attorney, Agent, or Firm*—Alston & Bird LLP

(57) ABSTRACT

Quaternary ammonium compounds having at least two fiber reactive sites and at least two dye reactive sites, and processes for making and using the same are disclosed. The compounds of the invention can advantageously be used in a cellulosic fabric pretreatment process to allow anionic dyeing without requiring salt to exhaust or drive the dye into the cellulosic fiber.

11 Claims, No Drawings

SALT FREE DYEING OF CELLULOSIC FIBERS WITH ANIONIC DYES

FIELD OF THE INVENTION

This invention relates to compounds and processes for using the same to improve the dyeability of textile fibers and fibrous assemblies. More particularly, the present invention relates to quaternary ammonium compounds and processes for using the same to dye cellulosic fibers and fibrous assemblies with anionic dyes without the use of salt.

BACKGROUND OF THE INVENTION

Many dyestuffs are rendered water-soluble by the incorporation of anionic groups into the dye molecule. However, the surface of cellulosic substrates is also negatively charged, and thus tends to repel anionic dyestuffs. Therefore, prior to the instant invention, virtually all dyes classified as anionic required some level of salt to speed the dyeing process.

Specifically, in a typical anionic dyeing process, the dye and the cellulosic substrate (cotton, rayon, etc.) are placed into a hot water bath, in which the cellulosic substrate swells. Salt is then added to the water to "salt" the dye out of solution and into the fiber. Indeed, conventional anionic dyeing processes for cellulosic fibers can employ significant amounts of salt, such as sodium chloride or sodium sulfate, as a dyebath exhausting agent. However, use of salts in dyeing can result in environmental problems relating to disposal of the exhausted dyebath.

Fiber reactive quaternary ammonium compounds have been used in conjunction with anionic dyes to increase various dyeing characteristics (such as color, color fastness, and the like). Salt free dyeing of cellulosic substrates has also been reported. For example, U.S. Pat. Nos. 5,330,541 and 5,489,313, both to Hall et al., report the use of a quaternary ammonium pretreat to eliminate salt in anionic dyeing of cellulose. In particular, the Hall et al. patents are directed to the use of an epoxy propyl trimethyl ammonium chloride pretreatment to eliminate salt in dyeing.

While these and other compounds can be useful in the dyeing of cellulosic fibrous assemblies, commercial use of such compounds has been limited. Such compounds can lack sufficient substantivity for the cellulose to provide subsequent dye color yield values comparable to those achieved when dyeing in the presence of salt. In addition, such processes can exhibit limited adaptability to various dye processes, and in particular to exhaustion or long liquor processes using conventional liquor ratios. In addition, it can be difficult to uniformly apply these compounds and/or control increased dyestuff rate-of-strike. Still further, these reagents can react sluggishly so that fixation of the compounds to a fabric must be conducted under relatively drastic conditions, for example, at elevated temperatures, high pH, and/or lengthy reaction times.

SUMMARY OF THE INVENTION

The present invention provides processes for dyeing textile fibrous assemblies having notable ecological advantages over conventional dyeing processes requiring the addition of salt to the dye-bath. Specifically, the present invention provides processes for improving the dyeability of textile fibrous assemblies containing cellulosic fibers without requiring a salt to drive the dyestuff into the cellulosic fiber. As a result, the expense, handling difficulties and disposal problems associated with salt can be eliminated. In addition, the dyes can exhaust completely to the fibrous assemblies and provide desirable deeper shades, thus maximizing dye utilization and allowing significant reductions in dyestuff usage. Further, the resulting textiles can be uniformly dyed and possess good colorfastness, thereby eliminating or minimizing the need for a fixative. Still further, the processes of the invention can be used with a variety of dyeing techniques, such as pad batch and exhaustion processes. Indeed, in contrast to prior salt-free dyeing techniques, the present invention allows the use of conventional liquor ratios in an exhaustion process. Thus the processes of the invention can also provide significant advantages in efficiency and cost as compared to conventional dyeing processes.

In the invention, fibrous assemblies comprising cellulosic fibers are treated with an aqueous composition comprising a novel highly substantive fiber reactive cationic compound of the formula (I) below:

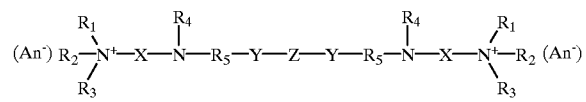

wherein:
$R_1$, $R_2$, and $R_3$ each are independently selected from the group consisting of $C_1$ to $C_{20}$ alkyl, $C_5$–$C_{12}$ cycloalkyl, and $C_6$–$C_{10}$ aryl, each of which is optionally substituted by 1–3 halogen, amino, hydroxyl, $C_1$–$C_4$ alkoxy or $C_1$–$C_4$ alkyl; or $R_1$ and $R_2$, together with N, form a 5, 6 or 7 membered heterocyclic ring, such as pyrrolidine, pyrrolidone, piperidine, morpholine, piperazine and the like, or form a 5, 6, or 7 membered heterocyclic aromatic ring such as pyridine, pyrrole, pyrimidine, imidazole, nicotinamide and the like, wherein each of said heterocyclic ring or heterocyclic aromatic ring may be optionally substituted by one or more hydroxyl, amine, amide, carboxyl, carbonyl or $C_1$–$C_4$ alkyl; or $R_1$, $R_2$, and $R_3$, together with N, form a bridged heterocyclic ring, such as quinuclidine, 1,4-diazabicyclo[2.2.2]octane (DABCO), and the like, optionally substituted by one or more hydroxyl, amine, amide, carboxyl, carbonyl or $C_1$–$C_4$ alkyl;

$R_4$ is hydrogen or $C_1$–$C_4$ alkyl;

X is $C_1$–$C_{10}$ alkylene, preferably substituted by hydroxyl;

$R_5$ is a 5 or 6 membered heterocyclic aromatic ring, preferably containing one or more nitrogen atoms, and having at least one reactive substituent capable of bonding with hydroxyl and amine groups;

Y is —NH—, —$NR_4$— or —S—;

Z is $C_6$–$C_{10}$ aryl, $C_5$–$C_{12}$ cycloalkyl, or $C_2$–$C_{10}$ alkylene; and $An^{(-)}$ is an anion.

Preferably, each $R_1$, $R_2$, and $R_3$ is $C_1$ to $C_4$ alkyl; $R_4$ is hydrogen; X is of the formula:

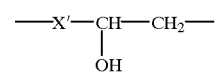

wherein $X^1$ is $C_1$–$C_{10}$–alkylene; $R_5$ is a triazine ring substituted with at least one halogen; each Y is —NH— or —$NCH_3$—; and Z is benzene. In an especially preferred embodiment of the invention, the compound has the formula

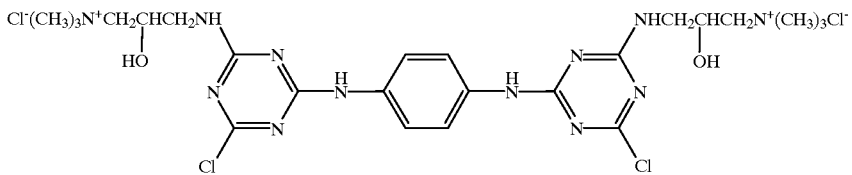

The cellulosic substrate is also treated with a suitable alkaline agent, such as sodium carbonate, under conditions sufficient to allow the pretreatment compound to covalently react with the cellulosic fibers of the fabric. The cationic reactant and alkaline agent can be applied to the fabric simultaneously or sequentially.

The fabric can then be dyed using a variety of anionic dyes, such as fiber reactive dyes, direct dyes, sulfur dyes, and vat dyes, using various dyeing techniques. Because the compounds of the invention can exhibit pronounced reactivity with hydroxyl groups of the cellulosic fibers, the compounds of the present invention can be applied under mild conditions. Accordingly, the process can be carried out at lower temperatures, lower pH values, and/or shorter reaction times than that required for prior fixing agents, such as those noted above which include an epoxy group as the reactive radical. In addition, such pretreated fibrous assemblies can be dyed using an exhaustion process with conventional process conditions. Further, the dyestuffs are substantially fully exhausted onto the fibrous assembly, resulting in a dyed material having good, uniform color and colorfastness. The remaining dye-bath effluent is substantially colorless (water-white) and free from undesirable salts, contaminants and the like.

Compounds of Formula (I) above are also provided in another aspect of the invention. The compounds of the invention can exhibit improved substantivity for cellulosic fibers as compared to traditional quaternary amines, in particular low molecular weight quaternary amines such as epoxy propyl trimethyl ammonium chloride. Due to its high substantivity, the compound can be applied to the cellulosic fibers under so-called long-liquor conditions, and the treated cellulosic fibers can subsequently be dyed with, for example, reactive dyes having water solubilizing groups such as sulphonate groups, without salt additions to the dyebath. In addition, the compounds allow use of a wider range of commercial process equipment to pretreat the fiber, while maintaining superior results. Thus, conventional dyeing procedures, equipment and routings can be used. In particular, the results achieved with the compound of the instant invention are superior to those previously possible with the use of conventional quaternary amines applied from conventional long-liquor exhaustion dyeing processes.

The present invention also provides cellulosic fibrous assemblies having a fiber reactive cationic compound of Formula (I) bound to the hydroxyl sites of the cellulosic fibers thereof, and processes for making the compounds of the invention.

DETAILED DESCRIPTION OF THE PREFERRED EMBODIMENTS

The present invention will be described more fully hereinafter in connection with illustrative embodiments of the invention which are given so that the present disclosure will be thorough and complete and will fully convey the scope of the invention to those skilled in the art. However, it is to be understood that this invention may be embodied in many different forms and should not be construed as being limited to the specific embodiments described and illustrated herein. Although specific terms are used in the following description, these terms are merely for purposes of illustration and are not intended to define or limit the scope of the invention.

The fiber reactive cationic compounds of the invention have at least two fiber reactive sites and, in a preferred embodiment, also have at least two dye reactive sites. The compounds have the formula

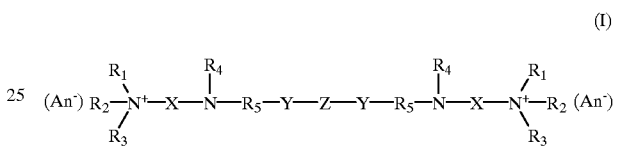

wherein:

$R_1$, $R_2$, and $R_3$ each are independently selected from the group consisting of $C_1$ to $C_{20}$ alkyl, $C_5$–$C_{12}$ cycloalkyl, and $C_6$–$C_{10}$ aryl, each of which is optionally substituted by 1–3 halogen, amino, hydroxyl, $C_1$–$C_4$ alkoxy or $C_1$–$C_4$ alkyl; or $R_1$ and $R_2$, together with N, form a 5, 6 or 7 membered heterocyclic ring such as pyrrolidine, pyrrolidone, piperidine, morpholine, piperazine and the like, or form a 5, 6, or 7 membered heterocyclic aromatic ring such as pyridine, pyrrole, pyrimidine, imidazole, or nicotinamide, and the like, all of which may be optionally substituted by one or more hydroxyl, amine, amide, carboxyl, carbonyl, or $C_1$–$C_4$ alkyl; or $R_1$, $R_2$, and $R_3$, together with N, form a bridged heterocyclic ring, such as quinuclidine, 1,4-diazabicyclo[2.2.2]octane (DABCO), and the like, optionally substituted by one or more hydroxyl, amine, amide, carboxyl, carbonyl or $C_1$–$C_4$ alkyl;

X is $C_1$–$C_{10}$ alkylene, preferably substituted by hydroxyl;

$R_5$ is a 5 or 6 membered heterocyclic aromatic ring, preferably containing one or more nitrogen atoms, and having at least one reactive substituent capable of bonding with hydroxyl and amine groups;

Y is —NH—, —NR$_4$— or —S—;

Z is $C_6$–$C_{10}$ aryl, $C_5$–$C_{12}$ cycloalkyl, or $C_2$–$C_{10}$ alkylene; and An$^{(-)}$ is an anion.

Preferably, each $R_1$, $R_2$, and $R_3$ is $C_1$ to $C_4$alkyl; $R_4$ is hydrogen or $C_1$–$C_4$ alkyl; X is

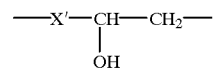

wherein X' is $C_1$–$C_{10}$–alkylene, preferably methylene; $R_5$ is a 6 membered heteroaryl selected from the group consisting of pyridine, pyrimidine, quinoxaline and triazine, preferably triazine, substituted with halogen; each Y is —NH— or —NCH$_3$—; and Z is benzene. Exemplary anions include anions of both organic and inorganic acids, and include without limitation chloride, bromide, sulfate, phosphate, tetrafluoborate, and the like. Also included are anions of acid alkyl esters of inorganic acids, such as the methosulphate and ethosulphate ions.

A particularly preferred compound of the invention has the formula

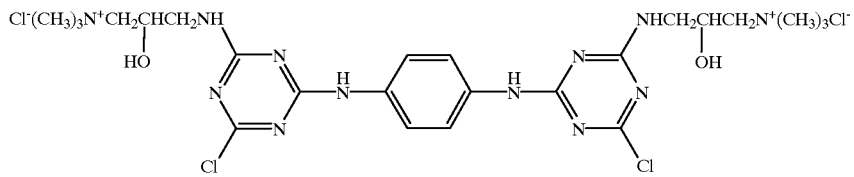

As used herein, the term "alkyl" means straight, branched or cyclic hydrocarbon, optionally substituted with one or more substituents, such as but not limited to, 1–3 halogen, amino, hydroxyl, C$_1$–C$_4$ alkoxy, C$_1$–C$_4$ alkyl, and the like. "Heterocycle" or "heterocyclic" means a 5, 6 or 7 membered ring without aromatic character and at least one ring atom which is not carbon, optionally substituted with one or more substitituents, such as but not limited to hydroxyl, amine, amide, carboxyl, carbonyl, C$_1$–C$_4$ alkyl, and the like. "Aryl" means one or more aromatic rings, each of 5 or 6 carbon atoms, optionally substituted with one or more substituents, such as but not limited to, 1–3 halogen, amino, hydroxyl, C$_1$–C$_4$ alkoxy, C$_1$–C$_4$ alkyl, and the like. Multiple aryl rings may be fused, as in naphthyl or unfused, as in biphenyl. "Heterocyclic aromatic," or heteroaryl, is an aryl group which can include 5, 6 or 7 members and further can contain from one to four N, O, or S atoms(s) or a combination thereof, optionally substituted at one or more of the carbon or nitrogen atom(s) with C$_1$–C$_4$ alkyl, or a carbon atom in the heteroaryl group together with an oxygen atom form a carbonyl group, or which heteroaryl group is optionally fused with a phenyl ring. Heteroaryl also may optionally be substituted with one or more substituents, such as but not limited to, hydroxyl, amine, amide, carboxyl, carbonyl, C$_1$–C$_4$ alkyl, and the like. For example, when R$_1$ and R$_2$, together with N, form a heterocyclic aromatic ring, the heterocyclic aromatic wrong can be a 5, 6 or 7 member heterocyclic ring. Also as an example, R$_5$ is a 5 or 6 member heterocyclic aromatic ring. Heterocyclic aromatic includes, but is not limited to, 5-membered heteroaryls having one hetero atom (e.g., thiophenes, pyrroles, furans); 5 membered heteroaryls having two heteroatoms in 1,2 or 1,3 positions (e.g., oxazoles, pyrazoles, imidazoles, thiazoles, purines); 5-membered heteroaryls having three heteroatoms (e.g., triazoles, thiadiazoles); 6-membered heteroaryls with one heteroatom (e.g., pyridine, quinoline, isoquinoline, phenanthrine, 5,6-cycloheptenopyridine); 6-membered heteroaryls with two heteroatoms (e.g., pyridazines, cinnolines, phthalazines, pyrazines, pyrimidines, quinazolines); 6-membered heteroaryls with three heteroatoms (e.g., 1,3,5-triazine); and 6-membered heteroaryls with four heteroatoms. "Alkylene" includes alkylene optionally substituted with one or more substitutents, such as but not limited to, 1–3 halogen, amino, hydroxyl, C$_1$–C$_4$ alkoxy, C$_1$–C$_4$ alkyl, and the like. "Halogen" means chloride, fluoride, iodide or bromide.

The compounds of the invention can be prepared by condensing an amine of the formula

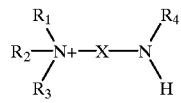

wherein each R$_1$, R$_2$, R$_3$, R$_4$ and X have the meanings defined above, with a 5 or 6 membered heterocyclic aromatic compound, preferably a nitrogen containing heteroaryl compound such as a triazine, having at least three reactive substituents capable of bonding with hydroxyl and amine groups. Preferably the reactive substituents are halide, more preferably chloride. As will be appreciated by the skilled artisan, at least one of the reactive substitutes reacts with the amine group to attach the heterocyclic aromatic ring to the amino group and form a reactive heterocyclic quaternary derivative of the formula

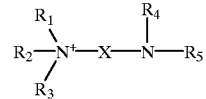

(II)

wherein R$_1$, R$_2$, R$_3$, R$_4$, R$_5$ and X are as defined above. Thereafter, two molecules of the resultant reactive heterocyclic quaternary derivative are coupled using a suitable bridging compound, such as p-phenylene diamine or ethylene diamine. The bridging compound is substituted with at least two nucleophilic substituents capable of linking or coupling two molecules of the quaternary derivative via reaction with a reactive substitutent of R$_5$ to form the multi-functional quaternary agents of Formula (I).

The reaction steps are conducted under conditions of pH, time and temperature sufficient to synthesize the compounds of the invention. Preferably, the condensing step is conducted at a pH of about 4 to about 8, more preferably about 6.5 and a temperature of about 0 to about 15° C., more preferably about 0 to about 5° C. The coupling step is preferably conducted at a pH of about 4 to about 8, more preferably about 6.5, and a temperature of about 30 to about 50 ° C., more preferably about 35 to about 40° C.

The reagents (amine, heterocyclic aromatic compound and di-amino bridging compounds) can either be prepared using commercially available compounds or are known in the art. Exemplary amines include without limitation synthesized reagents such as 1-amino-2-hydroxy-3-trimethyl ammonium propane, as well as commercially available reagents such as 1-amino-3-trimethyl ammonium propane, 1-amino-3-dimethyl ethyl ammonium propane, 1-amino-3-diethyl methyl ammonium propane, and the like.

Exemplary heterocyclic aromatic compounds are noted above. Preferably the heterocyclic aromatic compound is a trihalogenated symmetrical triazine, such as cyanuric chloride and cyanuric bromide. The compound can include reactive substituents other than halide, such as thiosulphato, sulphonate, and the like. A preferred aromatic bridging group is phenyl, substituted with hydroxy, thio or amino groups as the nucleophilic substituents. Representative alternative bridging groups include aliphatic diamines, such as $H_2N-(CH_2)_n-NH_2$, wherein n is 2–5; cycloaliphatic diamines, such as cyclohexane diamine; and aliphatic thioamines, such as $HS-(CH_2)_n-NH_2$, wherein n is 2–5.

In one particularly preferred aspect of the present invention, N— (3-chloro-2-hydroxypropyl) trimethylammonium chloride is first converted to its epoxide form, 2–3 epoxy propyl N-trimethylammonium chloride, by reaction with sodium hydroxide. The epoxide and its precursor are known and are commercially available from Dow Chemical Company. The epoxide is then reacted with ammonia to form the novel compound, 1-amino-2-hydroxy-3-trimethyl ammonium propane (AHTAPC), shown below:

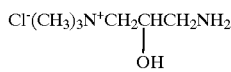

AHTAPC is then condensed with cyanuric chloride to yield the novel reactive dichloro-s-triazine quaternary derivative given below:

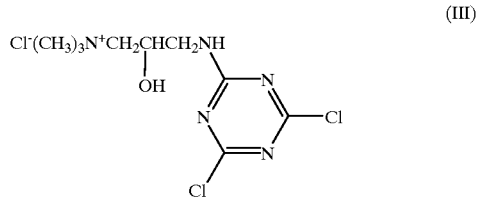

Two of the dichloro-s-triazine molecules are then coupled together via their reaction with p-phenylenediamine to yield the novel bifunctional monochlorinated heterocyclic quaternary ammonium compound shown below:

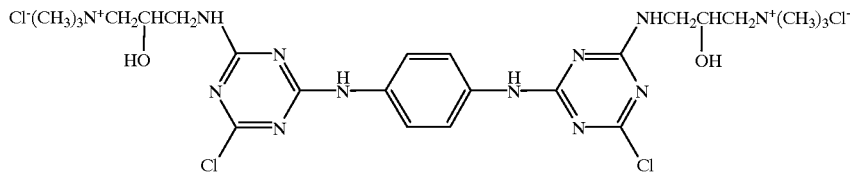

The water soluble, fiber reactive cationic compounds of the invention can be used in the pretreatment and dyeing of fibrous assemblies. The process is used with fibrous assemblies formed from yarns comprised of cellulosic fibers including cotton, linen, flax, viscose, cotton blends such as cotton/polyester blends, and the like. In addition, this process is also useful on other polyhydroxyl polymers such as polyvinyl alcohol. The fibrous assemblies dyed according to the invention can be greige (untreated) fibrous assemblies that have not been desized, scoured, or bleached prior to pretreatment. The process of the invention can also be used with fibrous assemblies treated to remove sizing or other processing agents. As used herein the term "fibrous assemblies" includes without limitation woven, nonwoven and knit fabrics, fibers, yarns, and the like.

In the process of the invention, the fabric is initially treated with a pretreatment composition comprising the fiber reactive bifunctional monohalogenated heterocyclic quaternary compound of the invention. The treating step may be accomplished by any suitable method. Preferably, the fiber reactive bifunctional monohalogenated heterocyclic quaternary compound of the invention is applied to the fabric via an exhaustion process, based on a liquor ratio ranging from about 5:1 to 50:1 and preferably about 10:1 or higher.

The compound of the invention can be applied to the fabric in amounts of about 2% to about 10% OWF (on weight fabric), and preferably about 3% to about 6% OWF. In addition, a suitable alkaline fixing agent is also applied to the fabric. Any of the known alkaline fixing agents known in the art can be used, including, but not limited to, sodium carbonate, sodium bicarbonate, sodium hydroxide, and the like, and mixtures thereof. The alkaline agent can be used in conventional amounts, typically about 5 to about 40 g/L, and preferably about 10 to about 20 g/L. The amount of alkaline fixing agent present in the pretreatment composition is sufficient to allow the quaternary ammonium compounds to penetrate the waxes, oils, and/or sizing agents which may be present on the cellulosic fibers and to promote significant ionization of the hydroxyl groups on the cellulosic fibers to form an adequate number of nucleophilic cellulosate anions and allow covalent bonding with the reactive substituents of the pretreatment compound.

The fiber reactive cationic compound of the invention and the alkaline agent can be applied simultaneously or sequentially. In one aspect of the invention, the fabric is treated with an aqueous pretreatment solution containing the fiber reactive cationic compound at a temperature from about 10 to about 100° C. The temperature is raised over 30 units, preferably to at least about 70° C., or higher, and held at this elevated temperature for up to 30 minutes. Alkali is then added to the bath and the fabric is maintained at a temperature ranging from about 60 to about 100° C. for about 20 to about 60 minutes.

In an alternative embodiment, the cellulosic fibrous assembly is treated with the reactive heterocyclic quaternary derivative of formula (II). In a preferred alternative embodiment, the reactive heterocyclic quaternary derivative is the bihalogenated heterocyclic quaternary amine given in formula (III). Milder pretreatment conditions may be employed when applying the derivative of formula (III) as a pretreatment, rather than formula (I). In this alternative embodiment, fabric is treated with an aqueous pretreatment solution containing the bihalogenated heterocyclic quaternary amine at a temperature from about 10 to 30 ° C. The temperature is then raised to 40 to 50° C. and allowed to equilibrate for 15 to 20 minutes. A sufficient amount of mild alkali, such as sodium carbonate, is then added to the bath and the fabric is maintained at a temperature ranging from about 40 to 50° C. for about 20 to 60 minutes.

The reactive heterocyclic quaternary derivative (II) may be applied by any suitable method, including both padding and substantive application processes. Non-substantive processes include pad batch, pad dry, pad steam, spraying, or immersing.

The pretreatment composition can contain other additives as known in the art, for example, a rheology modifying agent such as an antimigrant. Suitable rheology modifying agents include high molecular weight polymers such as high molecular weight polyacrylamide polymers having molecular weights of six million or higher. In addition, the pretreatment composition can include a wetting agent. Exemplary wetting agents include soaps, alcohols, fatty acids, and other agents that facilitate the absorbance of the aqueous components onto the fabric. For examples of well-known wetting agents that may be useful in the present invention, reference may be made to *Surface Active Agents and Detergents*, Vol. I and II by Schwartz, Perry and Burch; and U.S. Pat. No. 4,465,619 to Boskamp. Particularly preferred wetting agents are nonionic wetting agents such as alkyl phenol ethoxylates, linear alcohol ethoxylates, and fatty acid ethoxylates. The composition may further include small amounts of other conventional additives.

At the end of the pre-treatment process, the cationized fibrous assemblies can be removed and washed to remove unreacted fiber reactive cationic compound. For example, the fibrous assemblies can be washed with cold water for about 5 to about 30 minutes, and preferably about 10 minutes.

The pre-treated, washed fibrous assemblies are then dyed with an anionic dye. Any of the types of anionic dyes known in the art can be suitably employed in this process. Preferably, the dyestuffs include at least one dye selected from the group consisting of direct dyes, premetallized dyes, acid dyes, sulfur dyes, vat dyes, pigment dyes, reactive dyes and natural dyes. The specific dyestuffs used may be selected by those skilled in the art depending upon the type of fabric used, the particular color desired and other considerations. For example, with fibrous assemblies containing cellulosic fibers, such as cotton, direct dyes, fiber reactive dyes, acid dyes, vat dyes, sulfur dyes and/or pigment dyes may be used. Examples of suitable direct dyes include Direct Red 24, Direct Red 79, Direct Red 80, Direct Blue 189, Direct Blue 191.

In a preferred embodiment, the dye employed is a reactive dye. Fiber reactive dyes are characterized by the presence of electrophilic substituents, such as double bonds or heterocyclic halogens, which react with nucleophilic groups, such as hydroxyl groups. Examples of suitable fiber-reactive dyes include monochlorotriazine dyes (Procions® H dyes from BASF), vinyl sulfone dyes (Remazol® dyes from Dystar), difluorochloropyrimidine dyes (Levafix® E-A dyes from Dystar), monofluorotriazine dyes (Cibacron® F dyes from Ciba), modified monochlorotriazine dyes (Drimarene® X-N dyes from Clariant), monochlorotriazine-vinyl sulfone difunctional dyes (Sumifix Supra dyes from Sumitomo), dichlorotriazine dyes (Procion® Mx dyes from BASF), dichloroquinoxaline dyes (Levafix® dyes from Dystar), trichloropyrimidine dyes (Drimarenes X dyes from Clariant), bifunctional monochlorotriazine dyes (Procion® H-EXL dyes from BASF) and bifunctional monofluorotriazine dyes (Cibacron LS from Ciba).

Most shades with a properly balanced formula will be fully exhausted onto the fabric. The dyestuffs may be applied by any method, including various methods of exhaust dyeing and pad dyeing, as is known in the art.

In one embodiment of the invention, dyestuffs are introduced into a dyebath on a very slow, gradual basis. Preferably, the dyestuffs are introduced over a period of at least 5 minutes. When the dyestuffs are added, the dye-bath preferably has a temperature of about 40° C., and a liquor to goods ratio of about 10:1 or higher. Once the dyestuffs have been added, the washed, pretreated cotton fabric is placed in the dye-bath and the dye-bath is heated to its boiling temperature for time appropriate for the dye to exhaust onto the fabric. Typically, about 60 minutes is required to exhaust the dye onto the fabric. If the dye is a reactive dye, fixation is induced by adjusting the pH of the dyebath to a range of between 7 to 12, preferably 9.

In one example, Procion Red HE-3B, a fiber reactive dye, is employed at a 10:1 liquor ratio, along with sufficient 0.2 M disodium hydrogen phosphate to provide a starting pH of 9. The result is a cotton fabric, pre-treated using a long liquor process, dyed without the use of salt, which possesses a significantly higher color yield than untreated fibrous assemblies dyed with the traditional salt/alkali process. As an added benefit, use of the pretreatment compound of the instant invention allows milder dyeing conditions to be utilized with fiber reactive dyes. Conventional reactive dyeing requires a strongly alkaline environment, such as pH 10.5, to sufficiently activate the cellulose to react with the dyestuff. The present pretreatment compound provides a much more active nucleophilic site, in addition to the other benefits enjoyed from its cationic properties. This heightened nucleophilicity enables use of lower pHs, in the range of 7–9, to be used in reactive dyeing in the present invention.

In an alternative embodiment, a pretreated polyester/cotton fabric can be dyed with minor modifications to the normal disperse dyeing process to yield similar results. In the present invention, reactive dye and disperse dyes are introduced at 30° C. at pH 7.5 and the bath raised to 130° C. and maintained at this temperature for 30 minutes.

After the dye has been fully exhausted onto the fabric, and before the bath is drained, optional additives may be introduced into the bath. Specifically, additives such as anionic softeners, soil release agents, anti-stain agents, anti-static agents or the like can be added to the bath. The wet dyed fabric is subsequently removed from the dyeing apparatus and may then be finished by conventional methods.

The fabric which results from this process is characterized by having a cationic compound reacted with a cellulose hydroxyl group. In addition, in a preferred embodiment, the pretreatment compound, covalently bonded to the cellulosic fibers, also contains hydroxyl substituents. These pretreatment compound hydroxyl substituents are highly active and are readily available for subsequent covalent bonding with molecules containing electrophilic substitutents, such as reactive dyes having sulphonate or other electrophilic groups. Thus, in addition to cationic properties, the hydroxyl substituents of the pretreatment compound also provide reactive dye sites, which are distributed uniformly throughout the fabric. Although not wishing to be bound by any explanation of the invention, it is believed that the hydroxyl groups of the pretreatment compounds are more active, or nucleophilic, than expected, due to their close proximity to the quaternary amine substitutent on the pretreatment molecule. It is believed that the quaternary amine groups increase the ionic character of these nearby hydroxyl groups, a theory referred to as the "neighboring group effect." The ability to use milder reactive dyeing conditions in conjunction with the present invention is an example of a benefit from this effect.

Although not wishing to be bound by any explanation of the invention, it is believed that the anionic dyestuffs are electrostatically bound to the modified cellulose by the ionic attraction of the quaternary amine groups to the anionic dye. This is considered especially important in the use of direct dyestuffs, which are attracted to the cellulose surface by only weak forces, such as Van Der Waal's attraction. Reactive dyes are initially strongly attracted by the electrostatic interactions between their sulphonate group and the pretreatment cation, and diffuse out of the dyebath and into the fiber based on this attraction. After the reactive dye has penetrated the fiber, it readily reacts covalently with the highly nucleophilic hydroxyl group from the pretreatment compound, yielding enhanced fastness properties.

In addition, it has been further proposed that the strong positive charge of the ammonium group on the cationization compound of the instant invention neutralizes the negative charge on the fiber surface, which otherwise acts a barrier to the absorption of the negatively charged (anionic) dye. Due to this surface neutralization, the salt that was needed to obtain the shift is no longer required.

The following non-limiting examples further illustrate how textile fibrous assemblies are dyed in accordance with this invention. Responses used to determine the effect of pretreatment on salt free anionic dyeing included color yields and wash fastness. Color yields for the instant invention were determined by measuring their visually weighted Kulbelka-Munk (K/S) function, fk, using a Colorgen colorimeter under illuminant D65 using the 10 standard observer with specular component excluded and UV component included. An average of 4 measurements per sample was taken. Wash fastness was determined based on ISO CO6/2.

EXAMPLE 1
Synthesis of 1,4-Bis[2-chloro-4,(1-amino-2-hydroxy-3-trimethylammonium propane chloride)-s-triazine-6-amino] benzene A series of reactions were performed in which a quaternary amine epoxide was reacted to form a primary amine, this primary amine subsequently condensed with cyanuric chloride, and two molecules of this triazine derivative were linked together with half an equivalent of p-phenylenediamine.

A. Primary Amine Synthesis

A 65% w/v aqueous solution of N-(3-chloro-2-hydroxypropyl) trimethylammonium chloride (0.1 M, 28.9 g) (Tradename Quat 188 from Dow Chemical Co.) was converted to its epoxide form via the gradual addition (over 15–20 minutes) of a 50% w/v aqueous solution of sodium hydroxide (0.1 M, 8 g) at room temperature (this reaction takes 30 minutes after the addition). This epoxide was gradually added dropwise over a period of 1 hour to a stirred 32% aqueous solution of ammonia (1 M, 53.1 g). After the addition of the epoxide to the ammonia solution, the reaction mixture was stirred for a further 3 hours to yield the required product. The excess ammonia was removed on a rotary evaporator at 80° C. The product is referred to as AHTAPC, as noted above.

B. Synthesis of Bifunctional Monohalogenated Heterocyclic Quaternary Ammonium Compound cyanuric chloride (0.2 M, 37 g) was dissolved in acetone (200 ml) and gradually added dropwise (over 30–40 minutes) to an ice cold aqueous solution of AHTAPC (0.2 M). The pH of the solution was kept at 6.5 via the addition of 1 M sodium hydroxide, while the temperature of the solution/suspension was kept 5° C. When a constant pH had been achieved, the temperature of the reaction mixture was increased to 35–40° C. and half an equivalent of p-phenylenediamine (0.1 M, 10.8 g) was gradually added, the pH of the solution being maintained at 6.5 and the temperature between 35–40° C. The solution was stirred until a constant pH was achieved and the presence of free aromatic amine could no longer be detected using Erhlich's reagent (4-(dimethylamino)benzaldehyde). The acetone present was removed on a rotary evaporator at 70° C. to yield an aqueous solution having a solids content of 200 g/L of the cationisation agent 1,4-bis [2-chloro-4,(1-amino-2-hydroxy-3-trimethylammonium propane chloride)-s-triazine-6-amino] benzene dichloride. On cooling, the aqueous solution solidified, resulting in a gel that was readily water soluble.

To produce a pretreatment powder rather than a gel, the cationization agent may be precipitated as a pure solid via the addition of sodium thiocyanate. In order to process the cationization agent into usable form, the excess thiocyanate is removed by washing the product with acetone, excess water is then removed by running the washed precipitant through a filter press and drying the filter cake in an oven. Once dry, the filter cake is ground into a powder using a ball mill.

EXAMPLE 2
Conditioning the Fabric

The highly fiber substantive bifunctional monochloro-s-trizine derivative 1,4-bis [2-chloro-4,(1-amino-2-hydroxy-3-trimethylammonium propane chloride)-s-triazine-6-amino] benzene dichloride was applied to cotton via the following exhaustion process. A sample of cotton fabric was placed in a pretreatment bath containing 5% owf 1,4-bis[2-chloro-4,(1-amino-2-hydroxy-3-trimethylammonium propane chloride)-s-triazine-6-amino] benzene dichloride at a pH 7 using a 10:1 liquor ratio. The temperature in the pretreatment bath, initially at 20° C., was raised to 80° C. at a rate of 2.5° C./min. The pretreatment bath was allowed to equilibrate at 80° C. for 15 minutes, at which time 20 g/L of sodium carbonate was added, bringing the pH to 10.5. The addition of alkali allows covalent bonding of the pretreatment agent to the cotton. Subsequent to this addition, the pretreatment bath was allowed to equilibrate at 80° C. for 45 minutes. At the end of the pre-treatment process, the treated fibrous assemblies were removed and thoroughly washed with cold water.

EXAMPLE 3
Dyeing the Pretreated Fabric with Fiber Reactive Dyes

A. Procion Red HE-3B Fiber Reactive Dye

Pre-treated fibrous assemblies from Example 2 above were dyed with 2% owf Procion Red HE-3B fiber reactive dye via the following procedure. Pretreated cotton fabric (5 gm) was placed in a dyebath at 20° C. with 2% owf Procion Red HE-3, sufficient 0.2 M disodium hydrogen phosphate to bring the bath to a pH of 9 (approximately 20 ml), using a liquor ratio of 10:1. The dyebath temperature was then increased from 20° C. to 100° C. at a rate of 2.5° C./min. Once at temperature, the dyebath was allowed to equilibrate for 60 minutes. After dyeing, the fibrous assemblies were washed off at the boil for 15 minutes with a solution containing 2 gm/L of a nonionic alkyl ethoxylate surfactant, such as Sandozin NIE from Clariant Corp.

The resulting dyeing exhibited an fk value of 101.6. This indicates that the bifunctional monohalogenated heterocyclic quaternary ammonium compound of the instant invention may be used to pre-treat cotton fibrous assemblies from long liquor to yield subsequent dyeings which exhibit high color yields when dyed with reactive dyes in the absence of added electrolyte. The color yield achieved being higher than that obtained when cotton was modified using conventional processes. The color yield of untreated cotton dyed under these conditions was 10.88. Likewise, the color yield of cotton treated with a conventional quaternary amine, epoxy propyl trimethyl ammonium chloride, using a pad batch (40 g/l), was 89.

In addition, it is hypothesized that higher color yields and increased dyebath exhaustion than those obtained may be achieved if the fabric treated with 1,4-bis [2-chloro-4,(1-amino-2-hydroxy-3-trimethylammonium propane chloride)-s-triazine-6-amino] benzene dichloride was pre-boiled at pH8 for 15 minutes prior to its exhaust application.

B. Other Fiber Reactive Dyes

Cotton fabrics (5 g) were pre-treated with 5% owf of the cationization agent from Example 1 using the long liquor process of Example 2 and subsequently dyed with the various reactive dyes given below in the absence of added electrolyte following the process of Example 3A.

The following Remazol (Dystar Corp.) and Cibacron LS (Ciba) reactive dyes exhibited water-white dyebath exhaustion when applied to pre-treated fabrics in the absence of added electrolyte: Remazol Black B, Remazol Brilliant Green 6B, Remazol Yellow R, Remazol Red 3BS, Remazol Brilliant Blue R, Cibacron Green LS-3B, Cibacron Yellow LS-R, Cibacron Red LS-6G.

Further, the dyeings obtained exhibited wash fastness properties (based on ISO C06/2) similar to those exhibited by corresponding dyeings when applied via their commercial dyeing method in the presence of salt. The lightfastness properties of the dyed samples may optionally be improved by the addition of an effective amount of UV stabilizer to the dyebath, such as Uvinul MS 40, commercially available from BASF.

EXAMPLE 4
Dyeing the Pretreated Fabric with Direct Dyes

Cotton fibers pretreated with the compound from Example 1 and pretreated via the process of Example 2 were dyed with various direct dyes via the following procedure. The pretreated cotton fabric (5 gm) was placed in a dyebath at 20° C. with 2% owf direct dye at a pH of 7, using a liquor ratio of 10:1. The dyebath temperature was then raised from 20° C. to 100° C. at a rate of 2.5° C./min. Once at temperature, the dyebath was held for 60 minutes. After dyeing, the fabrics were washed off at the boil for 15 minutes with a solution containing 2 gm/L of an ethoxylated alcohol surfactant sold under the tradename Sandozin NIE from Clariant Corp.

The following direct dyes resulted in subsequent dyeings which exhibited water-white dyebath exhaustion when applied to pre-treated fabrics in the absence of added electrolyte: Solophenyl Black, Solophenyl Violet 4BL, Solophenyl Blue RFL, Solophenyl Blue GL (all available from Ciba). Although the direct dyeings did not exhibit as good wash fastness properties when subjected to ISO C06/2 wash fastness test, it is believed that such dyeings may be after-treated with suitable direct dye fixing agents to yield subsequent direct dyeings which have good wash fastness properties. Again, it is believed that light fastness properties of direct dyeings may be improved through the addition of a UV stabilizer.

EXAMPLE 5
Dyeing the Pretreated Fabric with Vat Dyes

Cotton fabrics pretreated with the compound from Example 1 and pretreated via the process of Example 2 were dyed with the solubilized vat dye Soledon Green XN (ICI) via the following procedure. The pretreated cotton fabric (5 gm) was placed in a dyebath at 40° C. which contained 1 ml/L Alexal WA-HS (ICI) and 0.5 g/L sodium carbonate, using a liquor ratio of 40:1. After allowing the bath to equilibrate for 5 minutes, 2 % owf Soledon Green XN and 0/25 gm sodium nitrite was added to the dyebath, which was then allowed to equilibrate for 45 minutes. The dyebath temperature was held constant throughout the dyeing. After dyeing, the fabric was treated in a dilute solution of sulphuric acid (5 g/L) for 15 minutes at room temperature, neutralized and washed with cold water. The dyeings were then washed off at the boil for 15 minutes with a solution containing 2 gm/L Sandozin NIE from Clariant Corp.

The subsequent vat dyeing on the pre-treated cotton exhibited a substantial improvement in color yield when compared with the conventional vat dyeing. A color yield, measured as a K/S function, of 27.3 was obtained for the dyeing on the pre-treated cotton compared with a value of 14.1 for a conventional vat dyeing. In addition, the vat dyeing on the pre-treated cotton exhibit excellent wash fastness properties when subjected to the ISO C06/2 wash fastness test.

EXAMPLE 6
Dyeing the Pretreated Fabric with Sulphur Dyes

Cotton fabrics pretreated with the compound from Example 1 and the process of Example 2 were dyed with Jarosol solubilized sulphur dyes (James Robinson) via the following procedure. The pretreated cotton fabric (5 gm) was placed in a dyebath at 100° C. which contained 2% owf solubilized sulphur dye and 1% OWF sodium sulphide, using a liquor ratio of 10:1. The dyebath temperature was held constant throughout the dyeing, and the fabric was allowed to equilibrate in the dyebath for 60 minutes. After dyeing, the fabrics were neutralized and thoroughly rinsed with cold water. The dyeings were after-treated for 15 minutes at 60° C. with an aqueous solution containing 5 g/L potassium dichromate, 5 g/L copper sulphate and 5 g/L acetic acid. The sulphur dyeings on the pre-treated cotton fabrics exhibited good wash fastness properties when subjected to ISO C06/2 wash fastness tests. The following sulphur dyes exhibited water-white exhaustion for the exhausted dyebaths: Jarosol Brown JGR, Jarosol Yellow JR, Jarosol Bordeaux JB.

EXAMPLE 7
Dyeing Polyester/Cotton Fabric

Polyester/cotton fabric pretreated with the compound from Example 1 via the process of Example 2 is dyed with the alkali clearable disperse dye using the following procedure. The pretreated polyester/cotton fabric (5 gm) is placed in a dyebath at 30° C. The pH of the dyebath is adjusted to 7 using a buffer such as VIRCOBUFFER 687 (The Virkler Company). The fiber reactive dye Procion Red HE 3B and the disperse dye are added to the dyebath, after which the dyebath is allowed to equilibrate for 10 minutes. The dyebath temperature is then raised to 130° C. at a rate of 2.5° C./min. The system is allowed to equilibrate at 130° C. for 20 minutes. The dyebath is then allowed to cool to 80° C. at a rate of 2.5° C./min. For dark shades, sodium carbonate is added and the system is allowed to equilibrate for 10 minutes following the addition. The bath is then drained, and the dyed sample is rinsed in cold water for 5 minutes.

The use of the dichloro-s-triazine compound of the instant invention results in a significant increase in process efficiency. In the instant invention a total dye cycle time of approximately 2 hours and 55 minutes is required for the pretreated polyester/cotton fabric, versus the 12 hour dye cycle used in the conventional dyeing of polyester/cotton fabrics.

These Examples indicate that the dichloro-s-triazine quaternary ammonium compound of the instant invention may be applied to cellulosic fibres via commercial exhaustion processes to yield subsequent salt free dyeings which exhibit similar color yields to corresponding dyeings obtained with conventionally treated cellulosic fibres. Also, milder dyeing conditions may be utilized when dyeing with reactive dyes.

In addition, pre-treated cotton of the instant invention can be readily dyed with solubilized vat dyes to yield a subsequent dyeing which exhibited a substantial improvement in color yield. The color yield of the dyeing on the pre-treated cotton was double that obtained on cotton fabric dyed via the commercial dyeing process. This is an added benefit, as vat dyes are relatively expensive and so such improvements in color yield would be extremely desirable. As a further benefit, polyester/cotton fabric can be dyed much more efficiently, allowing dyers to increase production significantly.

It has been proposed that the strong positive charge of the ammonium group on the cationization compound of the instant invention neutralizes the negative charge on the fiber surface, which otherwise acts a barrier to the absorption of the negatively charged (anionic) dye.

Due to this surface neutralization, the salt that was needed to obtain the shift is no longer required.

Many modifications and other embodiments of the invention will come to mind to one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A compound of the formula:

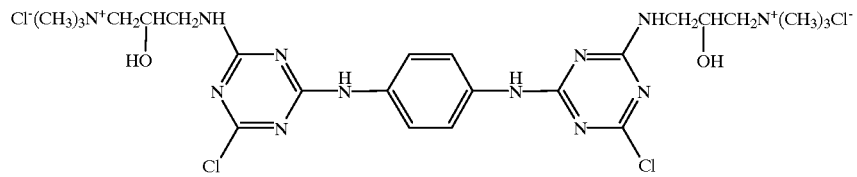

wherein:

$R_1$, $R_2$, and $R_3$ each are independently selected from the group consisting of $C_1$ to $C_{20}$ alkyl $C_5$–$C_{12}$ cycloalkyl, and $C_6$–$C_{10}$ aryl, each of which is optionally substituted by 1–3 amino, hydroxyl, $C_1$–$C_4$ alkoxy or $C_1$–$C_4$ alkyl; or $R_1$ and $R_2$, together with N, form a 5, 6 or 7 membered heterocyclic ring or a 5, 6, or 7 membered heterocyclic aromatic ring, optionally substituted by one or more hydroxyl, amino, amide, carboxyl, carbonyl, or $C_1$–$C_4$ alkyl; or $R_1$, $R_2$, and $R_3$, together with N, form a bridged heterocyclic ring, optionally substituted by one or more hydroxyl, amino, amide, carboxyl, carbonyl or $C_1$–$C_4$ alkyl;

$R_4$ is hydrogen or $C_1$–$C_4$ alkyl;

X is $C_1$–$C_{10}$ alkylene substituted by 1 to 3 hydroxyl;

$R_5$ is a triazinyl ring having at least one halogen substituent;

Y is —NH—, —NR$_4$—, —O—, or —S—;

Z is $C_6$–$C_{10}$ arylene, $C_5$–$C_{12}$ cycloalkylene, or $C_2$–$C_{10}$ alkylene; and $An^{(-)}$ is an anion.

2. The compound of claim 1, wherein each $R_1$, $R_2$, and $R_3$ is $C_1$ to $C_4$ alkyl; and $R_4$ is hydrogen.

3. The compound of claim 1, wherein X is

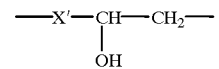

wherein $X^1$ is $C_1$–$C_8$ alkylene.

4. The compound of claim 1, wherein each Y is —NH— and Z is a benzene ring.

5. A compound of the formula:

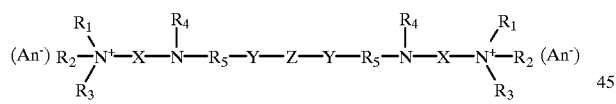

6. A process for making a quaternary amine compound, comprising the steps of condensing an amine of the formula

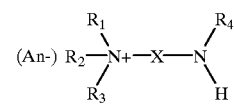

wherein:

$R_1$, $R_2$, and $R_3$ each are independently selected from the group consisting of $C_1$–$C_{20}$ alkyl, $C_5$–$C_{12}$ cycloalkyl, and $C_6$–$C_{10}$ aryl, each of which is optionally substituted by 1–3 amino, hydroxyl, $C_1$–$C_4$ alkoxy or $C_1$–$C_4$ alkyl; or $R_1$ and $R_2$, together with N, from a 5, 6 or 7 membered heterocyclic ring or a 5, 6, or 7 membered heterocyclic aromatic ring, optionally substituted by one or more hydroxyl, amino, amide, carboxyl, carbonyl, or $C_1$–$C_4$ alkyl; or $R_1$, $R_2$, and $R_3$, together with N, form a bridged heterocyclic ring, optionally substituted by one or more hydroxyl, amino, amide, carboxyl, carbonyl, or $C_1$–$C_4$ alkyl;

$R_4$ is hydrogen or $C_1$–$C_4$ alkyl;

X is $C_1$–$C_{10}$ alkylene substituted by 1 to 3 hydroxyl groups, with a triazinyl ring substituted by at least three halogen substituents, wherein one of said halogen substituents reacts with said amine to provide a reactive heterocyclic quaternary amine of the formula (III)

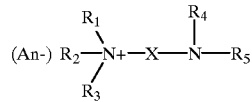

wherein $R_1$, $R_2$, $R_3$, $R_4$, and X are as defined above, and $R_5$ is the residue of said triazinyl ring and having at least two halogen substituents; and coupling two molecules of said reactive heterocyclic quaternary amine with a bridging compound selected from the group consisting of $C_6$–$C_{10}$ aryl, $C_5$–$C_{12}$ cycloalkyl, and $C_2$–$C_{10}$ alkyl and substituted with at least two groups selected from the group consisting of —OH, —SH, —NH$_2$, and —NR$_4$H to couple two molecules of said reactive heterocyclic quaternary amine of formula (III) via reaction with said halogen substituents of $R_5$, to form a quaternary amine compound of the formula

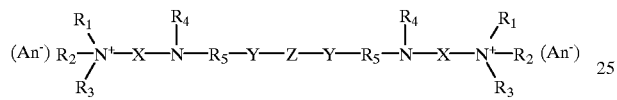

wherein $R_1$, $R_2$, $R_3$, $R_4$, X, and $R_5$ are as defined above, Y is —NH—, —NR$_4$—, —O—, or —S—; and Z is $C_6$–$C_{10}$ arylene, $C_5$–$C_{12}$ cycloalkylene, or $C_2$–$C_{10}$ alkylene.

7. The process of claim 6, wherein:

each $R_1$, $R_2$ and $R_3$ is $C_1$–$C_4$ alkyl, $R_4$ is hydrogen, and X is

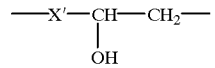

wherein $X^1$ is $C_1$–$C_8$ alkylene; and the two molecules of said reactive heterocyclic quaternary amine are reacted with benzene substituted with two groups selected from the group consisting of —SH, —NH$_2$, or —NR$_4$H.

8. The process of claim 7, wherein said amine is 1-amino-2-hydroxy-3-trimethylammonium propane chloride (AHTAPC), said triazinyl ring substituted by at least three halogen substituents is cyanuric chloride, and said substituted benzene is p-phenylene diamine.

9. The process of claim 6, wherein:

said condensing step is conducted at a pH of about 4 to about 8 and a temperature of about 0 to about 15° C.; and said coupling step is conducted at a pH of about 4 to about 8 and a temperature of about 30 to about 50° C.

10. The process of claim 9, wherein:

said condensing step is conducted at a temperature of about 0 to about 5° C. and a pH of about 6.5; and said coupling step is conducted at a temperature of about 35 to about 40° C., and pH of about 6.5.

11. The process of claim 8, further comprising prior to said condensing step the step of reacting 2–3 epoxy propyl N-trimethylammonium chloride with ammonia to form 1-amino-2-hydroxy-3-trimethyl ammonium propane chloride.

* * * * *